United States Patent
Bogacz et al.

(10) Patent No.: US 11,378,454 B1
(45) Date of Patent: Jul. 5, 2022

(54) SYSTEMS AND METHODS FOR USING MULTISPECTRAL IMAGERY FOR PRECISE TRACKING AND VERIFICATION

(71) Applicant: Illuscio, Inc., Culver City, CA (US)

(72) Inventors: Joseph Bogacz, Perth (CA); Robert Monaghan, Ventura, CA (US); Kevan Spencer Barsky, Ventura, CA (US)

(73) Assignee: Illuscio, Inc., Culver City, CA (US)

( * ) Notice: Subject to any disclaimer, the term of this patent is extended or adjusted under 35 U.S.C. 154(b) by 0 days.

(21) Appl. No.: 17/391,676

(22) Filed: Aug. 2, 2021

Related U.S. Application Data

(63) Continuation of application No. 17/131,325, filed on Dec. 22, 2020, now Pat. No. 11,079,278.

(51) Int. Cl.

| | |
|---|---|
| *A61B 5/00* | (2006.01) |
| *G01J 3/02* | (2006.01) |
| *G06K 9/00* | (2022.01) |
| *G06K 9/32* | (2006.01) |
| *G06K 9/62* | (2022.01) |
| *G01J 3/28* | (2006.01) |
| *G06V 10/24* | (2022.01) |
| *G01J 3/12* | (2006.01) |

(52) U.S. Cl.
CPC .......... *G01J 3/2823* (2013.01); *A61B 5/0075* (2013.01); *G01J 3/0229* (2013.01); *G06K 9/00536* (2013.01); *G06K 9/62* (2013.01); *G06V 10/24* (2022.01); *G01J 2003/1213* (2013.01); *G01J 2003/2826* (2013.01); *G06T 2207/10028* (2013.01)

(58) Field of Classification Search
None
See application file for complete search history.

(56) References Cited

U.S. PATENT DOCUMENTS

| | | | |
|---|---|---|---|
| 9,871,981 | B1 | 1/2018 | Lajevardi et al. |
| 2015/0051498 | A1 | 2/2015 | Darty |
| 2015/0369664 | A1 | 12/2015 | Garsha et al. |
| 2020/0311452 | A1* | 10/2020 | McConnell .......... G06K 9/2018 |

* cited by examiner

*Primary Examiner* — Patricia I Young
(74) *Attorney, Agent, or Firm* — Ansari Katiraei LLP; Arman Katiraei; Sadiq Ansari

(57) ABSTRACT

Provided is a multispectral imaging device for providing precise tracking and verification. The imaging device may configure a first filter for a sensor, and may determine first spectral properties of a target object based on a first image of the target object generated from visible light passing through the first filter onto the sensor. The imaging device may configure a different second filter for the sensor, and may determine second spectral properties of the target object based on a second image of the target object generated from the non-visible light passing through the second filter onto the sensor. The imaging device may align the second spectral properties of the second image with the first spectral properties of the first image, and may present the first spectral properties with the second spectral properties in a single composite image of the target object.

19 Claims, 10 Drawing Sheets

ND METHODS FOR USING
SYSTEMS AND METHODS FOR USING MULTISPECTRAL IMAGERY FOR PRECISE TRACKING AND VERIFICATION

CLAIM OF BENEFIT TO RELATED APPLICATIONS

This application is a continuation of U.S. nonprovisional application Ser. No. 17/131,325 entitled "Systems and Methods for Using Multispectral Imagery for Precise Tracking and Verification", filed Dec. 22, 2020 and issued as U.S. Pat. No. 11,079,278 on Aug. 3, 2021. The contents of application Ser. No. 17/131,325 are hereby incorporated by reference.

BACKGROUND

Computer imagery has the ability to detect beyond what the human eye is capable of. The additional data from computer imagery may enhance manufacturing processes with extremely narrow tolerances, surgery and/or other medical procedures (e.g., cancer treatment) where millimeter and event micrometer precision may be necessary for effective treatment, and/or differentiating a fake or reproduction from an original work.

DETAILED DESCRIPTION OF PREFERRED EMBODIMENTS

The following detailed description refers to the accompanying drawings. The same reference numbers in different drawings may identify the same or similar elements.

Provided are systems and methods for using multispectral imagery to provide precise tracking, mapping, and/or verification. In some embodiments, an imaging device may use different filters to capture different spectral properties of an imaged object using coherent and noncoherent light across different bands of the electromagnetic spectrum beyond just the visible light range and/or frequencies. The imaging device may map the different spectral properties to other image, positional, and/or other data, thereby increasing the points of reference to an exact location, providing sub-millimeter ("mm") accuracy and precision for identifying an exact location, and/or providing multispectral data with which to identify a feature at the exact location.

In some embodiments, the mapping may include layering and/or embedding the multispectral data to produce a composite image that enhances the visible light visualization of an object. For instance, the mapping may include embedding the multispectral data into the data points of a point cloud. The point cloud may present the multispectral data and/or other data via a single set of data points that may be manipulated to differentiate specific data points of interest. In other words, the point cloud representation may not simply layer captured data from a first spectral range that the imaging device captures with a first spectral filter over data from a second spectral range that the imaging device captures with a second spectral filter. Instead, the point cloud may provide a single unified view of the multispectral data. Moreover, the imaging device may distort, skew, and/or otherwise modify the multispectral data when storing the multispectral data to the point cloud so that the point cloud may accurately map the multispectral data in three-dimensional ("3D") space and/or may present the multispectral data with proper depth.

In some embodiments, the mapped multispectral data may be presented in an augmented reality display and/or other display to provide clear real-time visualization beyond the visible light range and/or frequencies, and/or to improve the accuracy and/or precision of a human actor. Here again, the imaging device may distort, skew, and/or otherwise modify the multispectral data to track movement, orientation, and/or positioning of the augment reality display, and/or to present the multispectral data at exact locations on a non-uniform object or surface.

Figure 1:
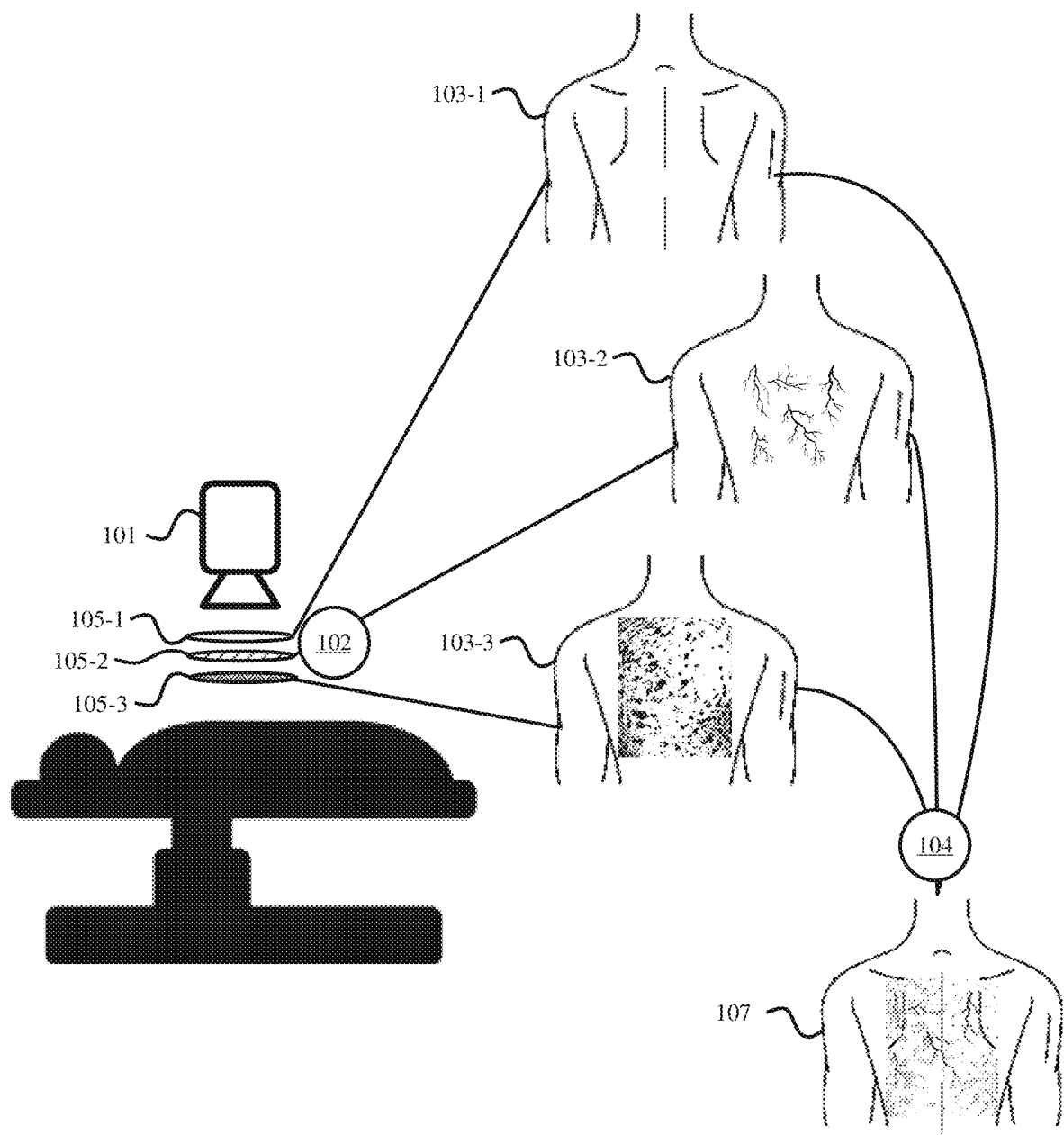
FIG. 1 illustrates an example of providing precise tracking from generating and mapping multispectral properties of a target object in accordance with some embodiments presented herein.

FIG. 1 illustrates an example of providing precise tracking from generating and mapping multispectral properties of a target object in accordance with some embodiments presented herein. As shown in FIG. 1, imaging device 101 may be statically positioned over an object, and may capture (at 102) three different images 103-1, 103-2, and 103-3 (sometimes collectively referred to as "images 103" or individually as "image 103") of the same object using three different filters 105-1, 105-2, and 105-3 (sometimes collectively referred to as "filters 105" or individually as "filter 105") respectively. In some other embodiments, imaging device 101 may mounted on a rig that moves around the object in order to capture images 103-1, 103-2, and 103-3 of the object from different angles, and/or to produce point cloud or 3D representations for image 103-1, 103-2, and 103-3. In still some other embodiments, multiple imaging devices 101 may be positioned over and around the object, each imaging device may generate images 103-1, 103-2, and 103-3 of the object from offset positions in 3D space. In this example, the object may be a part of the human body, and images 103 may guide a surgeon in performing a medical procedure at an exact location on the human body.

First image 103-1 may correspond to an image that captures visible light and the surface of the imaged body. Specifically, first image 103-1 may correspond to a section of skin. Second image 103-2 may correspond to an image that captures infrared light and the spectral properties of the skin exposed by the infrared light. For instance, the infrared light may expose the network of veins and capillaries under the skin based on differences in temperature and/or thermal properties of the veins and capillaries to the surrounding skin. Third image 103-3 may correspond to an image that captures ultraviolet light and differences across the skin exposed by the ultraviolet light. The ultraviolet light may expose freckles (e.g., minute differences in skin melanin), aging features, and/or other skin variations that may not be detected with the human eye or with visible light. Imaging device 101 may use at least first filter 105-1 (e.g., a single red, green, and blue filter or individual red, green, and blue filters) to filter out light outside the 400-700 nanometer ("nm") or $(4*10^{14})$-$(7.5*10^{14})$ Hertz ("Hz") range of visible light and thereby capture first image 103-1. Imaging device 101 may use second filter 105-2 to filter out light outside the 25-2.5 micrometer ("µm") or $10^{13}$-$10^{14}$ Hz range of infrared light and thereby capture second image 103-2, and may use a third filter to filter out light outside the 400-1 nm or $10^{15}$-$10^{17}$ Hz range frequency of ultraviolet light and thereby capture third image 103-3. In some embodiments, imaging device 101 may use different coherent and noncoherent light sources when capturing each of first image 103-1, second image 103-2, third image 103-3, and/or other images.

Imaging device 101 may generate (at 104) composite image 107 from layering and/or embedding the different multispectral properties captured in images 103. In particular, composite image 107 may combine the multispectral data from the different images 103, and as a result, may provide a more detailed, accurate, and/or enhanced presentation of the imaged part of the body. In some embodiments, the spectral properties captured with each filter may be visually represented as a different set of features, with different coloring, with different icons, and/or differentiated via other visual means in composite image 107. For instance, infrared spectral properties may be presented using different gradations of red, and may be presented in composite image 107 at each point of the targeted object where imaging device 101 detecting infrared spectral properties with specific values (e.g., values within a specified range to indicate presence of specific structures, values indicative of certain temperatures, etc.). In some embodiments, composite image 107 may include a point cloud or 3D image that presents the multispectral properties captured by images 103 in 3D space, and/or that presents the multispectral properties with 3D positioning to match where those multispectral properties were captured on the 3D form of the imaged object (e.g., to present the multispectral properties in composite image 107 with the same curvature, depth, layering, etc. as found on the actual image object).

The added detail, accuracy, and/or enhanced visualization provided by composite image 107 relative to each individual image 103 may provide finer grain or more precise mapping of the imaged part of the body. Specifically, a medical practitioner or technician may have several additional points of reference with which to locate an exact position on the body using composite image 107 relative to what the medical practitioner or technician sees with his own eyes or what is presented in just first image 103-1 of the skin outer layer. In particular, high-resolution imagery of a body part may provide the medical practitioner or technician up to 2 mm accuracy, whereas composite image 107 may provide sub-one mm accuracy. Such accuracy may improve the likelihood of a successful medical procedure and/or result in less recovery time when targeting cancerous cells with chemotherapy and/or radiation, when performing surgery, and/or when performing other procedures in which the extent of damage to healthy cells is minimized as a result of the increased accuracy.

Figure 2:
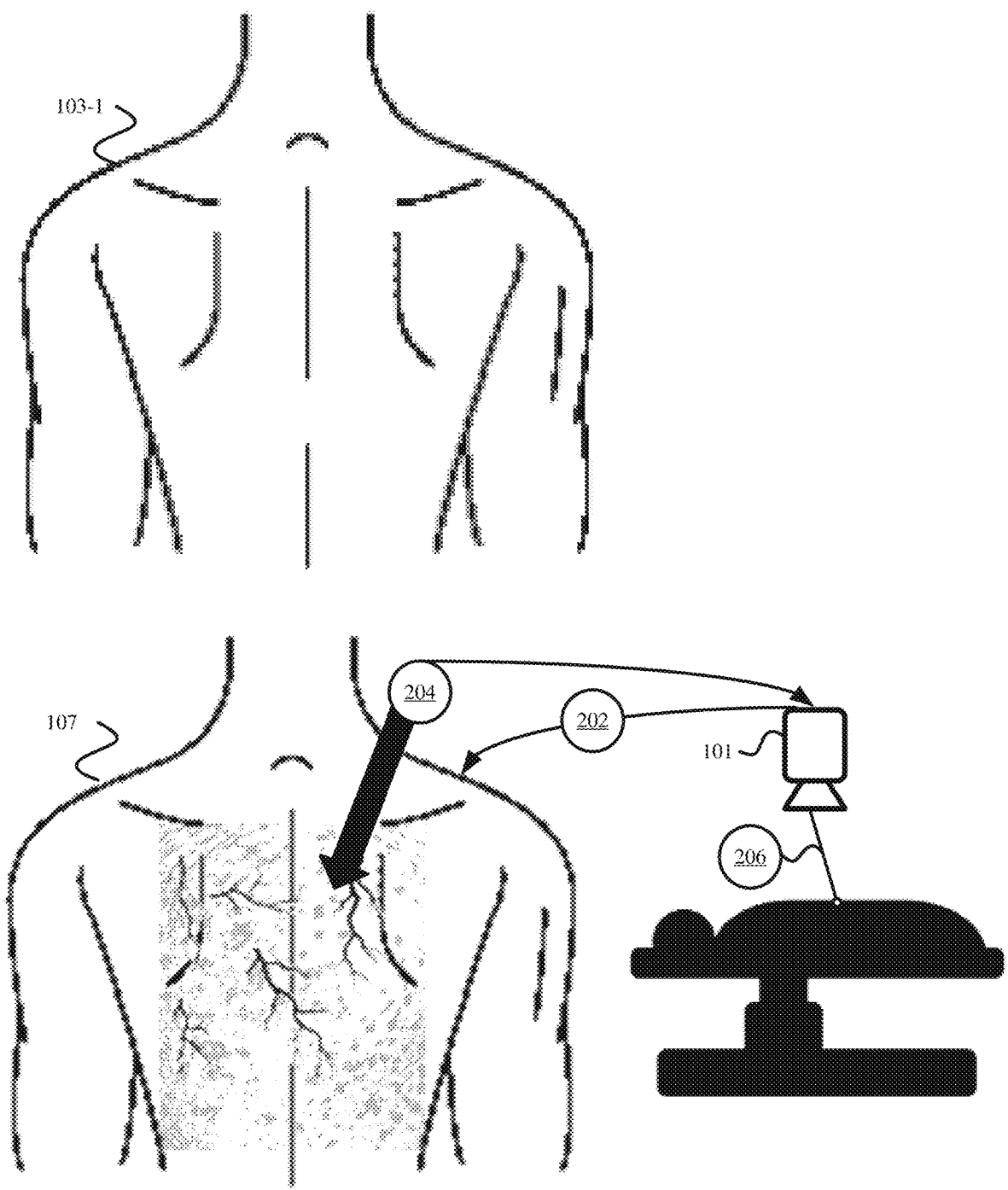
FIG. 2 provides an example that illustrates the additional points of reference provided by the multispectral properties in a composite image relative to another image that captures visible light or what is seen by the human eye in accordance with some embodiments presented herein.

FIG. 2 provides an example that illustrates the additional points of reference provided by the multispectral properties in composite image 107 generated by imaging device 101 relative to first image 103-1 that captures visible light or what is seen by the human eye in accordance with some embodiments presented herein. The multispectral properties may enhance the image detail, and may increase the accuracy for locating an exact location at which to perform a medical procedure.

In addition to presenting composite image 107, imaging device 101 may perform a mapping of composite image 107 back to the imaged object. In other words, points on the imaged object are linked to specific points in composite image 107 to control subsequent user or machine actions.

For instance, as shown in FIG. 2, imaging device 101 may present (at 202) composite image 107 to a user via a display. As noted above, composite image 107 may be presented as a 2D image or a 3D point cloud or image that presents the multispectral properties captured at different depths, planes, curves, etc. of the imaged object.

Imaging device 101 may receive (at 204) input from the user that marks an exact location on composite image 107. For instance, a medical practitioner may reference composite image 107 to mark an exact location at which to perform the medical procedure. Imaging device 101 may map the marked location in composite image 107 to a corresponding actual position on the imaged object. Imaging device 101 may direct (at 206) a laser light at the corresponding actual position on the imaged object so that the medical practitioner can locate the marked position from composite image 107 directly on the imaged object without having to refer back to composite image 107 or when composite image 107 is not presented in an augmented reality display. In some embodiments, imaging device 101 may capture depth information when imaging the object, may use the depth information when mapping the marked location in composite image 107 to the corresponding actual position on the imaged object, and may adjust the laser light and/or other indicator to account for any deviation between the marked location in composite image 107 and the corresponding actual position on the non-uniform imaged object.

In some embodiments, imaging device 101 may provide a direct mapping between composite image 107 and the imaged object. The direct mapping may include imaging device 101 providing composite image 107 to the medical practitioner via an augmented reality display that continually aligns composite image 107 with the corresponding imaged part of the body. In some such embodiments, imaging device 101 may be part of the augmented reality headset worn by a user. Imaging device 101 may provide a real-time and/or continuous layering of composite image 107 over a real-world view and/or a real-time camera feed, and may continually adjust and/or align composite image 107 based on movements of the headset and/or changes in the real-world view. Alignment of composite image 107 may include matching the depth, height, or 3D positioning of the real-world view with corresponding depth, height, or 3D positioning that are captured for different data points of composite image 107. In this manner, imaging device 101 may align what the user sees with landmarks and/or features that are exposed through the multispectral data of composite image 107. In some other embodiments, imaging device 101 may be a separate device from the augmented reality display, and imaging device 101 perform the multispectral imaging of the object separate from the presentation of composite image 107 in the augmented reality display. In some such embodiments, imaging device 101 may receive tracking information from the augmented reality display that identifies movement, orientation, and/or positioning of the augmented reality display, and may distort, skew, transform, and/or otherwise modify composite image 107 to present the multispectral data from composite image 107 according to tracked movement, orientation, and/or positioning of the augmented reality display. For instance, imaging device 101 may determine a relative position of the augmented reality display to the imaged object, may determine one or more transformations for aligning, skewing, distorting, and/or otherwise mapping composite image 107 onto the imaged object from the relative positioning of the augmented reality display, and may present composite image 107 in the augmented reality display with the one or more transformations. In other words, the one or more transformations correct for the difference in a first position at which imaging device 101 captures and/or generates composite image 107 of the imaged object, and a second position at which the augmented reality display is presenting the imaged object with the overlaid or embedded multispectral data from composite image 107. In still some other embodiments, imaging device 101 may use spectral highlights and/or other unique spectral features to track positioning and/or motion of the imaged object.

Figure 3:
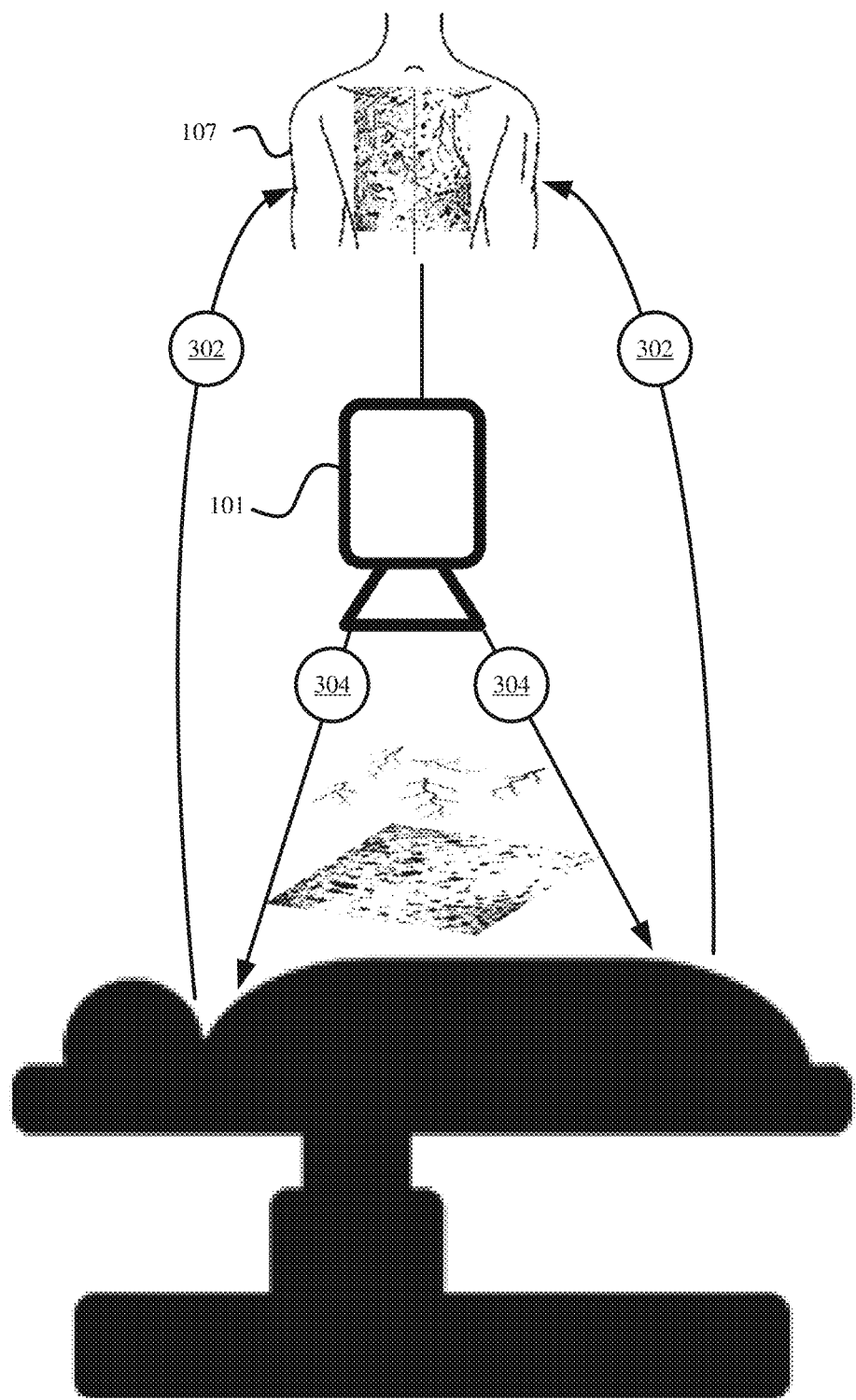
FIG. 3 illustrates an example of projecting spectral properties of an imaged object captured in a composite image onto the imaged object in accordance with some embodiments presented herein.

Instead of an augmented reality headset, imaging device 101 may provide the direct mapping by projecting composite image 107 onto the imaged object with spectral properties for specific points of composite image 107 being exactly aligned with corresponding points of the object from which the spectral data was acquired. FIG. 3 illustrates an example of imaging device 101 projecting spectral properties of an imaged object captured in composite image 107 onto the imaged object in accordance with some embodiments presented herein.

As shown in FIG. 3, imaging device 101 may generate (at 302) composite image 107 from imaging the target object with different spectral filters. Imaging device 101 may orient and/or otherwise align the multispectral properties from composite image 107 with corresponding points of the target object. In particular, imaging device 101 may perform image analysis to determine dimensions of composite image 107, and may use one or more transformations to match the multispectral properties from composite image 107 directly with corresponding points on the target object. The one or more transformations may include distorting, skewing, and/or otherwise modifying a two-dimensional ("2D") representation of composite image 107 onto a 3D form of the imaged object, or may include mapping a 3D representation of composite image 107 to corresponding locations and depths across the 3D of the imaged object. For instance, composite image 107 may correspond to a 3D point cloud with data points capturing the multispectral properties at different positions in 3D space that correspond to different positions at different planes, depths, or positions across the 3D form of the target object.

Imaging device 101 may overlay the multispectral data directly onto the target object using a high-resolution projector that projects (at 304) the multispectral properties at a particular point in composite image 107 to the corresponding location of the target object at which those multispectral properties were captured. Specifically, imaging device 101 may project (at 304) the multispectral properties by providing a visible light representation for non-visible spectral properties (e.g., infrared, ultraviolet, and/or other electromagnetic spectrum ranges outside the visible light spectrum) onto the target object. In this manner, the user may visualize the multispectral properties directly on the target object without having to wear a specialized headset or reference a display off and/or away from the target object.

In some embodiments, output from imaging device 101 (e.g., composite image 107) may be input directly to a controller of autonomous machinery and/or may be used to control movements of the autonomous machinery. For instance, imaging device 101 may be part of a sensory array of a robot. Composite images 107 from imaging device 101 may provide the robot with sensory input that the robot uses to move and/or to accurately position actuators, tools, and/or other components with sub-1 mm precision.

Figure 4:
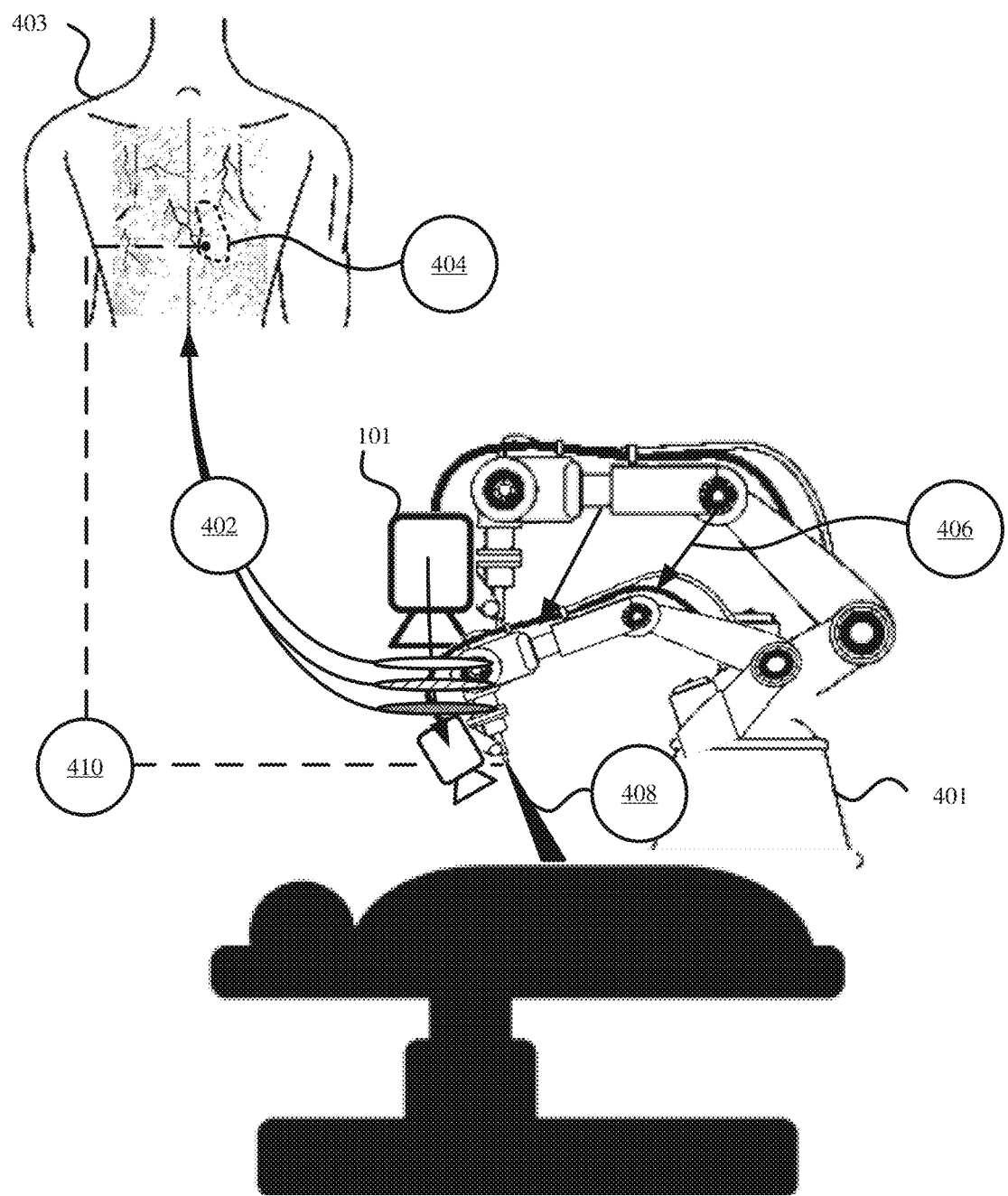
FIG. 4 illustrates an example of providing precise control of an automated tool based on the multispectral imaging of an object in accordance with some embodiments presented herein.

FIG. 4 illustrates an example of imaging device 101 providing precise control of automated tool 401 based on the multispectral imaging of an object in accordance with some embodiments presented herein. Specifically, automated tool 401 may be a laser for excising or burning away cancerous tissue without damaging healthy tissue, and the targeted object may be an exposed region within a patient's body. Imaging device 101 may directly control movement and/or firing of the laser.

Imaging device 101 may be attached to automated tool 401 or may be located off of automated tool 401. Imaging device 101 may generate (at 402) one or more composite images 403 of the object, may map the data points from composite images 403 to corresponding points of the actual object, and may identify (at 404) specific points corresponding to the cancerous tissue by using the multispectral properties to automatically differentiate the cancerous tissue from nearby healthy tissue. Alternatively, in some embodiments, a user may manually select the specific points or the region corresponding to the cancerous tissue.

Imaging device 101 may determine a current position of automated tool 401 relative to the specific points of cancerous tissue. In some embodiments, imaging device 101 may be positioned to capture a tip or end of automated tool 401 in composite images 403, and may determine the current position of automated tool 401 by comparing the position of automated tool 401 to the position of the specific points for the cancerous tissue. In some other embodiments, imaging device 101 may be centered about the tip or end of automated tool 401 such that the current position of automated tool 401 corresponds to the exact center of composite images 403.

Imaging device 101 may compute a set of movements with which to reposition and align automated tool 401 with the specific points of cancerous tissue, and may execute (at 406) the set of movements. Imaging device 101 may verify that automated tool 401 is correctly positioned by generating a new composite image 403 and detecting the position of automated tool 401 in the new composite image 403.

Once automated tool 401 is precisely aligned, imaging device 101 may activate (at 408) automated tool 401, and may precisely control automated tool 401 to engage only the specific points of cancerous tissue by continually comparing (at 410) the position and engagement of automated tool 401 against the multispectral mapping of the object in composite image 403.

Figure 5:
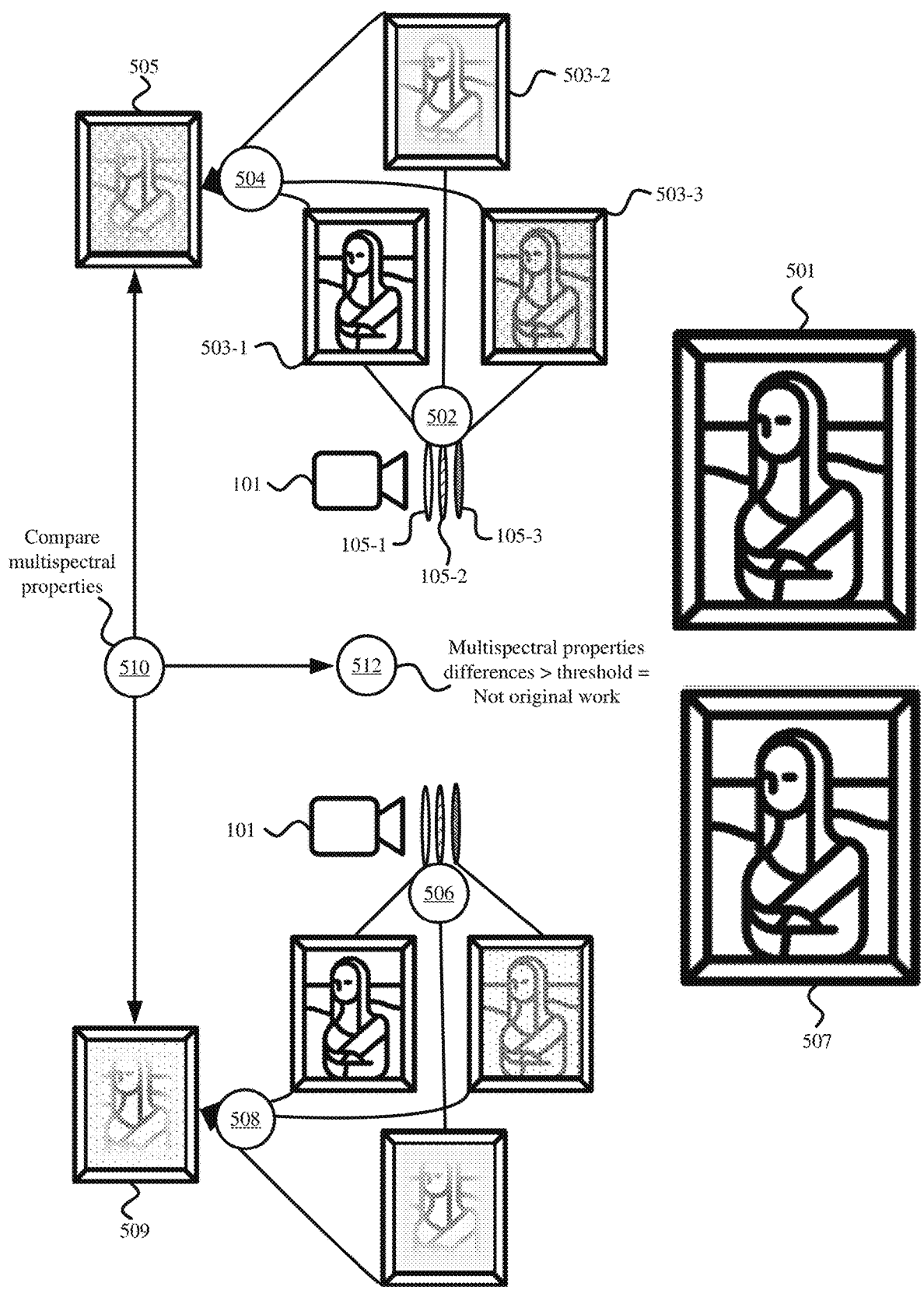
FIG. 5 illustrates an example of verifying authenticity of a work using the mapped multispectral data in accordance with some embodiments presented herein.

In some embodiments, the mapped multispectral data may be used to verify the authenticity of an object or work. FIG. 5 illustrates an example of verifying authenticity of a work using the mapped multispectral data in accordance with some embodiments presented herein.

As shown in FIG. 5, imaging device 101 may be statically positioned over original work 501, and may capture (at 502) multiple images 503-1, 503-2, and 503-3 (sometimes collectively referred to as "images 503" or individually as "image 503") of original work 501 using different filters 105 at a first time. Original work 501 may include art (e.g., a painting, sculpture, pottery, etc.), photography, manuscripts, and/or other physical articles or objects that may be reproduced.

With each filter 105 and image 503, imaging device 101 may capture different multispectral data for different visible and non-visible properties of original work 501. Specifically, imaging device 101 may identify different attributes of original work 501 using different multispectral light or different coherent and noncoherent light.

In some embodiments, each of images 503-1, 503-2, and 503-3 may be captured at different angles or offset positions in order to capture the multispectral data with depth information. In other words, image 503-1 may be captured at different angles or offset positions in order to determine the depth, plane, and/or other 3D positioning for the multispectral data.

Imaging device 101 may generate (at 504) reference image 505 for original work 501 based on the multispectral data captured by images 503. For an oil painting, reference image 505 may include the coloring of the oil painting falling within a first range of the electromagnetic spectrum (e.g., visible light spectrum), the translucency of the paint that is exposed by a second range of the electromagnetic spectrum (e.g., ultraviolet spectrum), the texture, thickness, or density of the paint that is exposed by a third range of the electromagnetic spectrum (e.g., X-ray spectrum), the roughness of the canvas and/or the layering of the paint atop the canvas as measured with a fourth range of the electromagnetic spectrum (e.g., infrared spectrum), and/or other properties of the paint that are exposed in different electromagnetic spectrum ranges. Imaging device 101 may store reference image 505.

At a later second time, imaging device 101 may perform (at 506) a multispectral imaging of reproduced work 507, wherein reproduced work 507 is a reproduction or copy of original work 501. A skilled artisan may be able to make reproduced work 507 appear identical or nearly identical to original work 501 to the most discerning eye, especially when original work 501 is not available for a side-by-side comparison or only high-resolution images of original work 501 are available to compare against reproduced work 507. For instance, a lender may loan original work 501 to a third-party, and the lender may need to verify that original work 501 is being returned by the third-party and not a reproduction.

Imaging device 101 may use the different filters to capture different visible and non-visible spectral properties of reproduced work 507. Imaging device 101 may generate (at 508) composite image 509 based on the multispectral data captured from reproduced work 507.

Imaging device 101 may compare (at 510) composite image 509 to reference image 505 in order to verify whether reproduced work 507 is original work 501 or some reproduction, copy, and/or replica of original work 501. Imaging device 101 may compare (at 510) images 505 and 509 by comparing data for different multispectral properties of each image 505 and 509, and determining if the compared data from images 505 and 509 is within a threshold value of one another. In some embodiments, imaging device 101 may compare (at 510) the multispectral data at each captured data point of reference image 505 to the multispectral data at corresponding points of composite image 509.

By comparing (at 510) composite image 509 to reference image 505, imaging device 101 may detect differences that are not visible to the human eye even under magnification. For instance, imaging device 101 may detect that the texture of the canvas, thickness of the paint, elevation of the paint off the canvas, and/or other properties between reference image 505 and composite image 509 are different. Imaging device 101 may determine if the differences are greater than a threshold amount to account for tolerances of imaging device 101.

In response to detecting sufficient differences or a threshold amount of difference between composite image 509 of reproduced work 507 and reference image 505 of original work 501, imaging device 101 may determine (at 512) that reproduced work 507 is a fake, replica, unauthorized reproduction, and/or other copy of original work 501, and not original work 501. In some embodiments, may output (at 512) the detected differences as evidence.

Museums, galleries, and/or other holders of original works may use imaging device 101 to confirm that work that is loaned or temporarily placed in the custody of others is in fact returned and not substituted with a fake. Similarly, imaging device 101 may be used to verify the authenticity of original work 501 prior to a sale and/or transfer from one party to another. For instance, buyers may require proof-of-authenticity for the actual work being purchased which imaging device 101 may substantiate by comparing the multispectral properties of the work being purchased with the multispectral properties of the original work provided by the original artist. In a similar manner, imaging device 101 may verify the origin of a work. For instance, a limited set of lithographs of an original work may be authorized by an artist. The limited set of lithographs may be generated with particular machinery using particular inks, paints, and/or other materials. Imaging device 101 may precisely determine the particular inks, paints, patterning, and/or other materials used to generate the limited set of lithographs, and may therefore be able to detect a lithograph that is generated using different machinery and/or different materials.

In some embodiments, imaging device 101 may be used for archival purposes. In some such embodiments, imaging device 101 may precisely map visible light and non-visible light attributes of original work 501, and store those attributes for subsequent reference or research. For instance, reference image 505 of original work 501 may be shared amongst researchers or stored for historic purposes to record exact brush strokes, technique, paint, materials, and/or other attributes of original work 501. Researchers may compare the archived multispectral data for different works of the same artist to determine how the artist changed over time.

In some embodiments, the mapped multispectral data may be used to improve motion capture accuracy. Currently, motion capture technology relies on a grid-based mapping of an actor body and/or face, and using a set of cameras to track movements of data points within the mapped grid. Such motion capture may have the ability to accurately capture larger movements such as arm and leg movements, but may lack the accuracy to track nuanced movements from certain facial expressions.

With the multispectral imaging, imaging device 101 may produce a near infinite amount of data points with which to track large and microscopic movements. In particular, imaging device 101 may use visible light, infrared light, ultraviolet light, coherent light, noncoherent light, and/or other electromagnetic spectrum ranges to produce different sets of trackable spectral properties with which to track the positioning and movement of individual skin lines (e.g., wrinkles), minute differences in skin coloring, and/or other skin variances (e.g., moles, facial hair, skin texture, etc.). Alternatively, imaging device 101 may use specific spectral features to track the positioning and movements. For instance, imaging device 101 may track spectral highlights that are present at specific points based on the angle of illumination by the light source. Imaging device 101 may provide a real-time feed of the multispectral data to a motion capture device in order to precisely map the large and small movements to a digitally created object.

Imaging device 101 may be used in other fields and for other applications beyond those described above. For instance, imaging device 101 may be used to map the multispectral properties of different organic and nonorganic matter. In agriculture, the multispectral properties of organic fruits, vegetables, plants, etc. may be used to automatically ascertain the health, ripeness, and/or other qualities of the organic matter. In some embodiments, imaging device 101 may include a machine learning component that determines the peak ripeness of particular organic matter from different spectral properties that are obtained when imaging the particular organic matter with two or more of visible light, infrared light, ultraviolet light, coherent light, noncoherent light, and/or other electromagnetic spectrum ranges. Similarly, imaging device 101 may capture the multispectral properties of nonorganic matter in order to measure rigidity, strength, and/or other characteristics of the nonorganic matter. For instance, a manufacturing system may weld different pieces together, and imaging device 101 may automatically determine the strength and/or quality of the weld based on a multispectral imaging of the weld.

Figure 6:
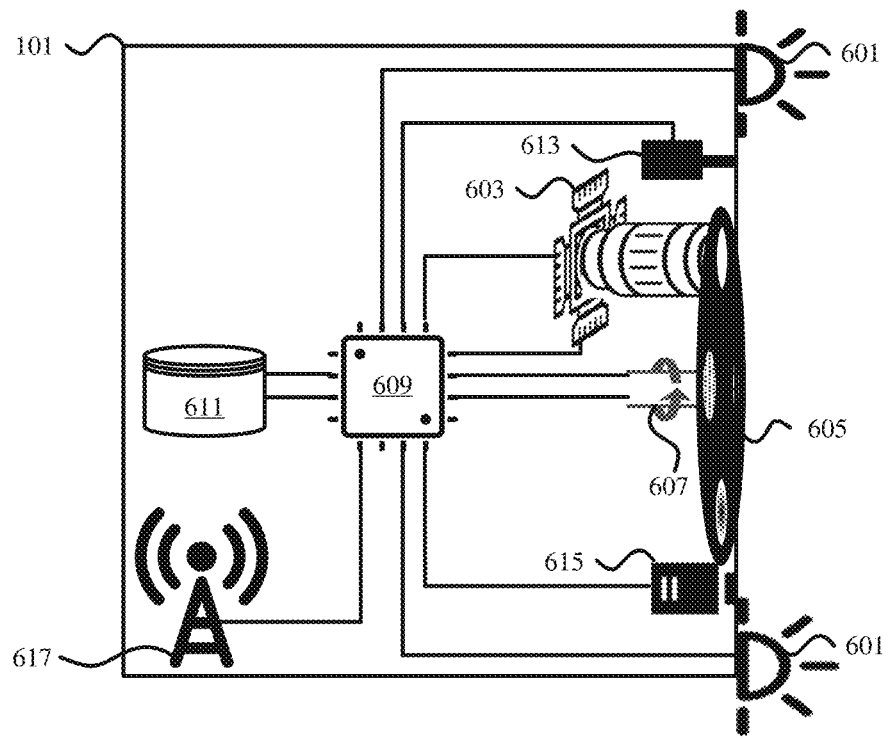
FIG. 6 illustrates components of an imaging device for performing the precise tracking, autonomous control, authentication verification, enhanced motion capture, and/or other functionality in accordance with some embodiments presented herein.

FIG. 6 illustrates components of imaging device 101 for performing the precise tracking, autonomous control, authentication verification, enhanced motion capture, and/or other functionality in accordance with some embodiments presented herein. Imaging device 101 may correspond to a specialized multispectral camera with one or more of multispectral light source 601, sensor 603, filters 605, rotation element 607, processor 609, storage 611, indicator 613, projector 615, and/or wireless radio 617.

Multispectral light source 601 may include one or more Light Emitting Diodes ("LEDs"), lasers, structured light, and/or other sources capable of generating light within various ranges or frequencies of the electromagnetic spectrum including at least infrared, visible, and/or ultraviolet light. Accordingly, multispectral light source 601 may include coherent and noncoherent light sources. A coherent light source may generate a beam of photons at the same frequency, wavelength, and/or phase. For instance, a coherent light source may include laser light. A noncoherent light source may generate photons that are out-of-phase, varying frequencies, and/or varying wavelengths. A noncoherent light source may include an LED. Imaging device 101 may switch between coherent and noncoherent light sources to better image and/or capture different spectral properties of an object. For instance, laser light may penetrate deeper through a top layer of organic matter, and may be used with one or more filters 605 to capture nonvisible spectral properties of the organic matter below the top layer, whereas visible light from an LED light source may capture different visible spectral properties of the organic matter at the top layer. Light source 601 may be powered by an external power source or an onboard battery.

Sensor 603 may include a monochromatic and/or another sensor for converting captured light and/or electromagnetic radiation into electrical signals. In some embodiments, sensor 603 may include a Charge-Coupled Device ("CCD") sensor or Complementary Metal-Oxide-Semiconductor ("CMOS") sensor. Sensor 603 may capture different spectral properties of an object that may be illuminated and/or exposed by light source 601. Filters 605 may restrict the light passing onto sensor 603, and may cause sensor 603 to measure and/or capture attributes of specific ranges and/or frequencies (e.g., visible, infrared, ultraviolet, and/or other electromagnetic spectrum) permitted by each filter 605.

In addition to capturing the multispectral properties of an imaged object, sensor 603 may be used to capture depth information. In particular, light source 601 may illuminate the surface of the imaged object with a structured light pattern. Sensor 603 may capture variations, distortions, and/or deviations of the structured light pattern on the object surface, and may compute depth and/or distance based on the variations, distortions, and/or deviations. For instance, sensor 603 may detect the height of paint over a canvas in a painting and/or the texture of the canvas based on measured variations, distortions, and/or deviations in the structured light pattern.

In some embodiments, sensor 603 may combine other imaging technologies such as LIDAR, X-Ray, Radar, and Computerized Tomography ("CT"), in order to obtain depth information for the imaged object. Accordingly, sensor 603 may include a three-dimensional ("3D") sensor that is used in generating 3D point cloud imagery.

Filters 605 may include two or more filters that permit different electromagnetic spectrum bands to pass to sensor 603. In other words, each filter 605 may focus a particular range of wavelengths and/or frequencies onto sensor 603, thereby allowing sensor 603 to measure the different spectral properties of an imaged object that are exposed in each filtered range of the electromagnetic spectrum. Filters 605 may include separate filters that pass through visible light, infrared, ultraviolet, X-ray, microwave, and/or other wavelengths or frequencies within the electromagnetic spectrum. In some embodiments, two or more filters 605 may be used to improve the capture of specific ranges of light and/or the electromagnetic spectrum. For instance, a first filter may be used to capture near infrared light, and a second filter may be used to capture far infrared light. Similarly, filters 605 may include separate filters to capture red, green, blue, cyan, magenta, and yellow light in the visible light spectrum. Each filter 605 may include a lens or piece of optical glass with a specialized or different coating that permits different ranges or frequencies of light or the electromagnetic spectrum to reach sensor 603.

Rotation element 607 may include a motor for rotating different filters 605 over or in front of sensor 603. By positioning different filters 605 over or in front of sensor 603, rotation element 607 may change the wavelengths and/or frequencies that are received and/or measured by sensor 603.

In some embodiments, imaging device 101 may omit rotation element 607, and may directly place different filters 605 over different photosites of sensor 603. For instance, a repeating sequence of different filters 605 may be positioned over photosites of sensor 603. The repeating sequence may include a first red filter over a first photosite, a second green filter over a second photosite that is directly adjacent to the first photosite, a third blue filter over a third photosite that is directly adjacent to the second photosite, a fourth infrared filter over a fourth photosite that is directly adjacent to the third photosite, and a fifth ultraviolet filter over a fifth photosite that is directly adjacent to the fourth photosite. This sequencing of filters may be repeated over each set of five consecutive photosites of sensor 603, and imaging device 101 may generate a composite image by combining the multi spectral data from each set of five consecutive photosites into a single data point of the composite image.

In some embodiments, imaging device 101 may replace rotation element 607 with a prism. The prism may divide light equally to two or more destinations. A different sensor 603 with a different filter 605 may be placed at each destination to measure different spectral properties of the filtered light.

Processor 609 may control light source 601 in emitting different light, may control rotation element 607 in placing different filters 605 over or in front of sensor 603, may control sensor 603 in capturing data as each filter 605 is positioned over sensor 603, and/or may combine different spectral data that is captured by different sensors 603 and/or photosites of sensor 603. Accordingly, processor 609 may synchronize operation of imaging device 101 components.

In some embodiments, processor 609 may process the data that is generated and/or captured by sensor 603 using different filters 605. For instance, processor 609 may capture an image with different spectral properties of an object using each filter 605 and/or different sets of photosites of sensor 603. In some embodiments, processor 609 may map the data from each image to a composite image, and/or may produce an overlaid or embedded presentation of the data. Accordingly, processor 609 may generate output with the different spectral properties that present the imaged object with additional data beyond what is observed by visible light. In some embodiments, processor 609 may produce a point cloud representation to provide a 3D visualization of the imaged object that includes the depth information and the multispectral data for each data point of the point cloud representation that corresponds to a different imaged part of the object.

Processor 609 may use storage 611 to store the captured images, the multispectral properties, composite images, and/or point cloud representations of an imaged object. Storage 611 may include volatile and/or non-volatile memory.

Processor 609 may control indicator 613. Indicator 613 may include a moveable laser light source or other moveable visual indicator with which imaging device 101 may identify an exact location on an imaged object with sub-mm precision. For instance, imaging device may generate a composite image that is presented on a separate display to a user. The user may reference the different spectral properties from the composite image to select a precise location at which to perform an action. Imaging device 101 may map the selection in the composite image to an exact position of the imaged object, and may illuminate the exact position with indicator 613.

Projector 615 may include a display device with which the spectral properties of an imaged object captured from non-visible light may be overlaid or presented on the imaged object. For instance, imaging device 101 may capture the infrared spectral properties of an imaged object. Rather than generate a composite image to display the spectral properties, imaging device 101 may map the composite image to a surface of the imaged object, and may present the infrared spectral properties at the mapped locations of the imaged object using visible light emitted from projector 615.

In some embodiments, imaging device 101 may control other devices based on wireless signaling issued from wireless radio 617. In particular, imaging device 101 may generate a composite image of an object, may determine an exact location at which to perform an action based on the multispectral properties from the composite image, may determine a position of an automated tool relative to the exact location on the object, and may issue a set of commands via wireless radio 617 to control the automated tool in performing the action at the exact location on the object.

As noted above, imaging device 101 may generate a composite image as a point cloud. The point cloud may include a set of data points for representing a 3D or volumetric object. The point cloud data points may differ from pixels of a two-dimensional ("2D") image, because certain regions of the point cloud may have no data points, lower densities of data points, and/or higher densities of data points based on varying amounts of visual information that is detected at those regions. In contrast, pixels of a 2D image have a uniform density and fixed arrangement that is defined by the resolution of the 2D image. Moreover, the point cloud data points may have a non-uniform placement or positioning, whereas the 2D image has pixel data for each pixel of a defined resolution (e.g., 640×480, 800×600, etc.).

Each point cloud data point or set of data points may correspond to a different sub-mm region of an imaged object. Point cloud data points may be layered atop one another with a first data point capturing the spectral properties for a particular location of the imaged object at a first depth, and a second data point capturing the spectral properties for the particular location at a different second depth. Accordingly, each point cloud data point may include positional and non-positional information.

The positional information may include coordinates within 3D space. For instance, each point cloud data point may include x-coordinate, y-coordinate, and z-coordinate data point elements that map to different x-coordinate, y-coordinate, and z-coordinate locations across the imaged object at which spectral data is captured by imaging device using one or more filters 605. Accordingly, there may be direct one-to-one correspondence between the positional information of each point cloud data point and each sub-mm region of the imaged object.

The non-positional data point elements may store the spectral data that is detected by imaging device 101 at a corresponding position of each data point in or on the object. For instance, the non-positional data point elements for a particular data point may provide visible light, infrared, ultraviolet, luminance, chrominance, reflectivity, hue, saturation, and/or other visible and nonvisible attributes or spectral properties for the sub-mm region on the object represented by that particular data point in the point cloud.

In some embodiments, each point cloud data point may be represented as an array. The array may include entries for the positional information (e.g., x, y, and z coordinates), and entries for the different multispectral data that is captured by sensor 603 when configured with a different filter of filters 605. Data points may have different non-positional data point elements. For instance, a first point cloud data point may include spectral data that imaging device captures at a first object position with a first filter and a second filter, and a second point cloud data point may include spectral data that imaging device 101 captures at a second object position with a third filter, but for which no spectral data is captured when imaging the object with the first filter and the second filter.

As noted above, the point cloud is a 3D representation and/or mapping for the multispectral properties of an imaged object. The distortion, skew, and/or other variation between the multispectral data at different depths may already be stored in the point cloud data points. Accordingly, when rendering the point cloud from different perspectives, imaging device 101 may adjust the multispectral data stored in the non-positional data elements based on the angle, perspective, and/or other positioning from which the point cloud is rendered.

Figure 7:
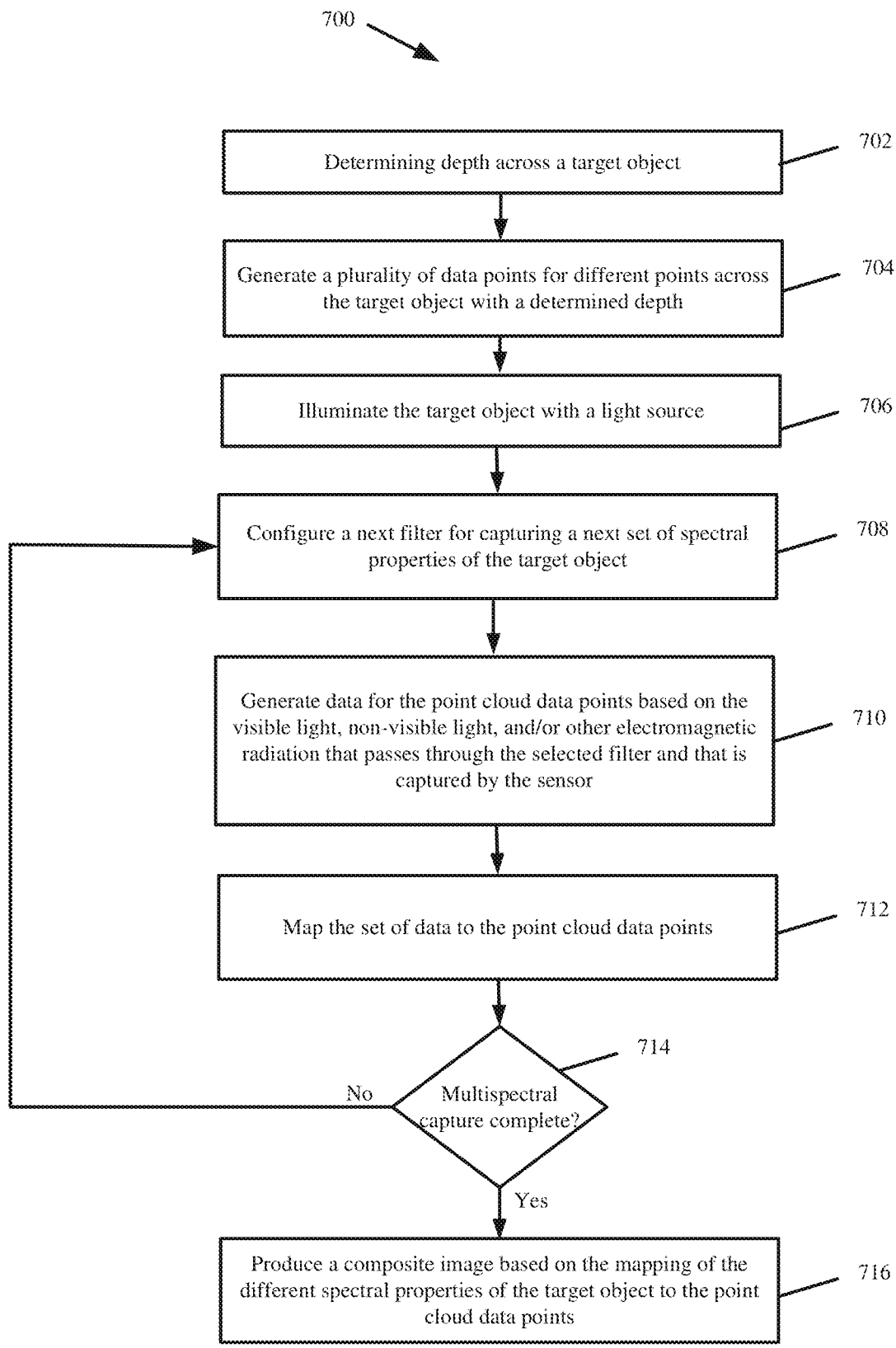
FIG. 7 presents a process for capturing the multispectral data with a point cloud in accordance with some embodiments presented herein.

FIG. 7 presents a process 700 for capturing the multispectral data with a point cloud in accordance with some embodiments presented herein. Process 700 may be performed by imaging device 101.

Process 700 may include determining (at 702) depth across a target object. Determining (at 702) the depth may include illuminating a structured pattern over the target object with light source 601, capturing the structured pattern over the target object with a camera and/or one or more images, and/or calculating different depths and/or distances across the target object based on variations, distortions, and/or deviations of the structured pattern.

Process 700 may include generating (at 704) a plurality of data points for different points across the target object with a determined (at 702) depth. Generating (at 704) the plurality of data points may include setting the positional data elements for each of the plurality of data points based on a computed amount of variation, distortion, and/or deviation in the structured pattern at the corresponding point of the target object. For instance, each pixel or photosite of sensor 603, for which a measure of the structured pattern is obtained, may be converted to a point cloud data point, and may be positioned within the point cloud according to the measured depth at that pixel or for that data point.

Process 700 may include gradually adding the spectral attributes of the target object to the point cloud with different filtered images or data captured by sensor 603. In particular, process 700 may include illuminating (at 706) the target object with light source 601. In some embodiments, light source 601 may control the illumination (at 706) of the target object by emitting different ranges of electromagnetic radiation (e.g., different light from the electromagnetic spectrum) at different times. Accordingly, illuminating (at 706) the target object may include illuminating the target object with visible and/or non-visible light and/or other electromagnetic radiation from the electromagnetic spectrum. For instance, process 700 may include illuminating (at 706) the target object with infrared light at a first time, visible light at a second time, ultraviolet light at a third time, etc. Alternatively, light source 601 may simply illuminate the target object with light in all desired ranges of the electromagnetic spectrum, and imaging device 101 may use filters 605 to measure the spectral properties of the target object in different ranges of the electromagnetic spectrum.

Process 700 may include configuring (at 708) a next filter 605 for capturing a next set of spectral properties of the target object. Configuring (at 708) the next filter 605 may include positioning and/or otherwise aligning the next filter 605 over sensor 603 so that only a specific range of electromagnetic radiation or light is permitted to pass through and be measured by sensor 603. In some embodiments, configuring (at 708) the next filter 605 may include activating rotation element 607 to physically move a filter 605 over or onto sensor 603. In some other embodiments, configuring (at 708) the next filter 605 may include electronically controlling a set of filters 605 in order to activate a particular filter 605 and deactivate other filters (e.g., setting the other filters to an entirely transparent or pass-through mode). In still some other embodiments, configuring (at 708) the next filter 605 may include activating and/or recording a measurement with a specific one of a set of sensors 603 (when a prism divides light between multiple sensors) and/or a set of photosites on a particular sensor 603 (when photosites of the particular sensor 603 include different filters 603) that receives filtered light and/or electromagnetic spectrum from the next filter 605.

Process 700 may include generating (at 710) a set of data for the point cloud data points based on the visible light, non-visible light, and/or other electromagnetic radiation that passes through the selected filter 605 and that is captured by sensor 603. In some embodiments, generating (at 710) the set of data may include measuring spectral properties at different points of the target object within a particular range or frequency of the electromagnetic spectrum passing through the next filter 605, with the different points of the target object corresponding to the plurality of data points generated for the point cloud representation of the target object.

Process 700 may include mapping (at 712) the set of data to the point cloud data points. In particular, imaging device 101 may populate a set of non-positional data elements of the point cloud data points with the set of data. The mapping (at 712) may include storing to a particular data point of the point cloud, the spectral data that is captured for the same physical point on the imaged object by one or more pixels or photosites of sensor 603 and/or one or more sensors 603 using different filters.

Process 700 may include determining (at 714) if the multispectral capture of the target object is complete. The multispectral capture of the target object is complete once the target object is imaged and the multispectral properties of the target objects are measured with each of a set of different filters.

In response to determining (at 714—No) that the multispectral capture of the target object incomplete, process 700 may include configuring (at 708) a next filter 605 and/or modifying the illumination of the target object with light source 601 based on the configured filter 605. For instance, light source 601 may turn off a first light and turn on a second light in order to change the electromagnetic spectrum range that is emitted from light source 601 and/or that is being used to illuminate the target object.

Process 700 may include generating (at 710) another set of data based on the different light or electromagnetic radiation that passes through the newly configured filter 605 and that is captured by a particular sensor 603, a set of photosites of the particular sensor 603, and/or one or more sensor 603 configured with the newly configured filter 605. Process 700 may again include mapping (at 712) the set of data to different non-positional data elements of the point cloud data points. In this manner, each point cloud data point may store the spectral properties at a particular point on the target object that are exposed and isolated using different filters for visible light, infrared light, ultraviolet light, and/or other ranges of the electromagnetic spectrum.

In response to determining (at 714—Yes) that the multispectral capture of the target object is complete, process 700 may include producing (at 716) a composite image for the target object based on the mapping of the different sets of data for the different spectral properties of the target object to the point cloud data points. In some embodiments, producing (at 716) the composite image may include rendering the point cloud to provide a visualized representation of the target object via the point cloud data points, and to further provide the different spectral properties of the target object that are captured using the different filters 605 and/or that are exposed when illuminating the target object with different ranges of electromagnetic radiation at different times (e.g., infrared light at a first time, visible light at a second, and ultraviolet light at a third time).

Figure 8:
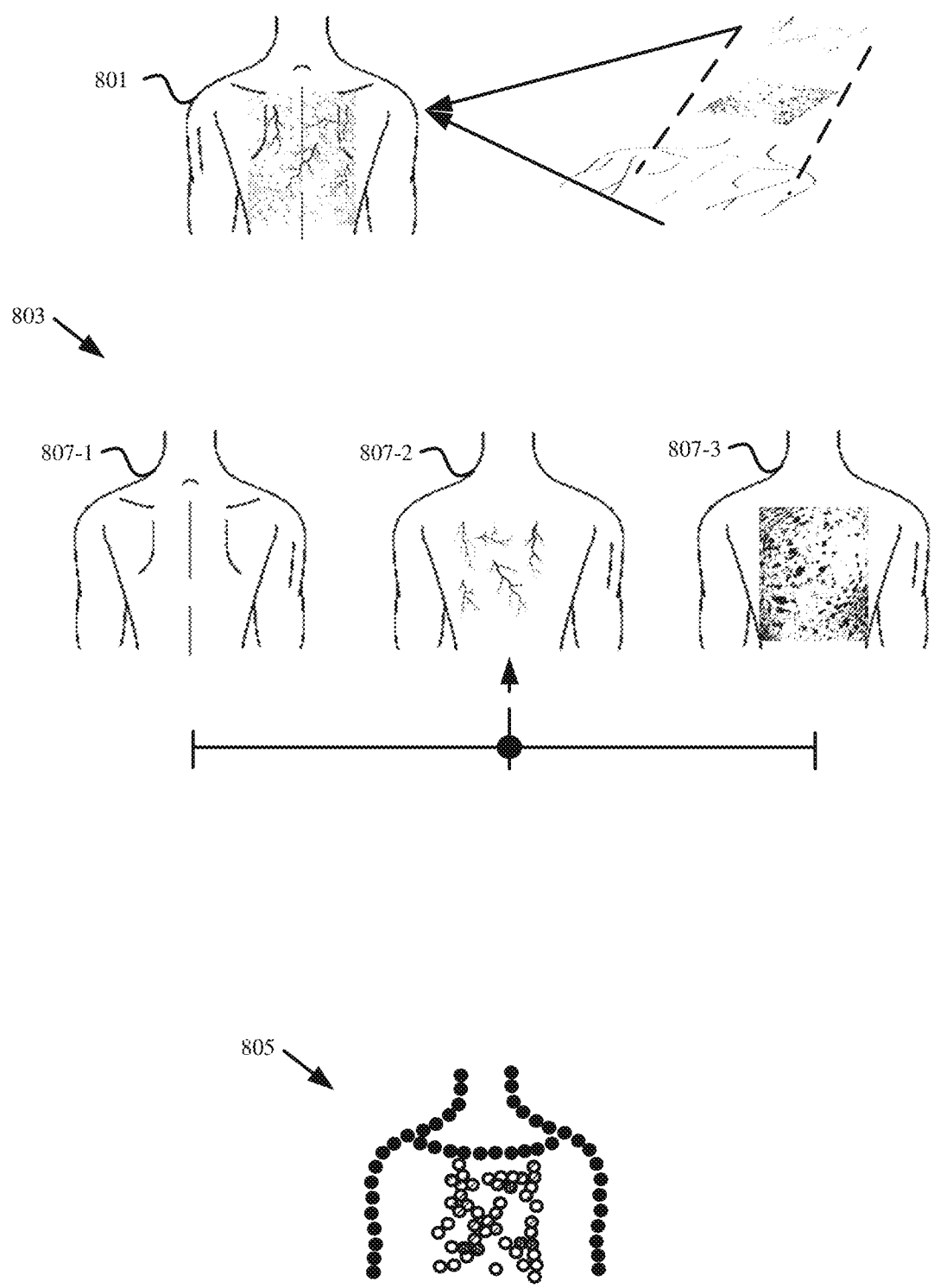
FIG. 8 presents examples of different composite images that may be produced in accordance with some embodiments presented herein.

FIG. 8 presents examples of different composite images 801, 803, and 805 that may be produced by imaging device 101 in accordance with some embodiments presented herein. First composite image 801 may include a single image that is overlaid with different layers representing the different spectral properties of the target object. For instance, first composite image 801 may present an image that is captured with visible light, and may overlay atop the image features, coloring, and/or other data that are exposed when capturing the infrared, ultraviolet, and/or other spectral properties of the target object.

Second composite image 803 may include a single image with an interactive slider or tool. The interactive slider may be used to change the spectral properties of the target object that are shown in the image. For instance, second composite image 803 may present first set of spectral properties 807-1 of the target object captured using a visible light filter when the interactive slider is at a first setting, different second set of spectral properties 807-2 of the target object captured using an infrared light filter when the interactive slider is at a second setting, and third set of spectral properties 807-3 of the target object captured using a ultraviolet light filter when the interactive slider is at a third setting.

Third composite image 805 may provide a point cloud rendering of the target object showing the different spectral properties with different data point visualizations and/or presentations. In particular, a data point may be colored or presented based on the combined set of spectral properties that were measured at the corresponding point on the target object.

In some embodiments, the composite image may be produced in combination with other images and/or feeds. In some embodiments, imaging device 101 may receive a CT, Positron Emission Tomography ("PET"), Magnetic Resonance Imaging ("MRI"), or other scan, and may enhance the scan with the multispectral data.

Figure 9:
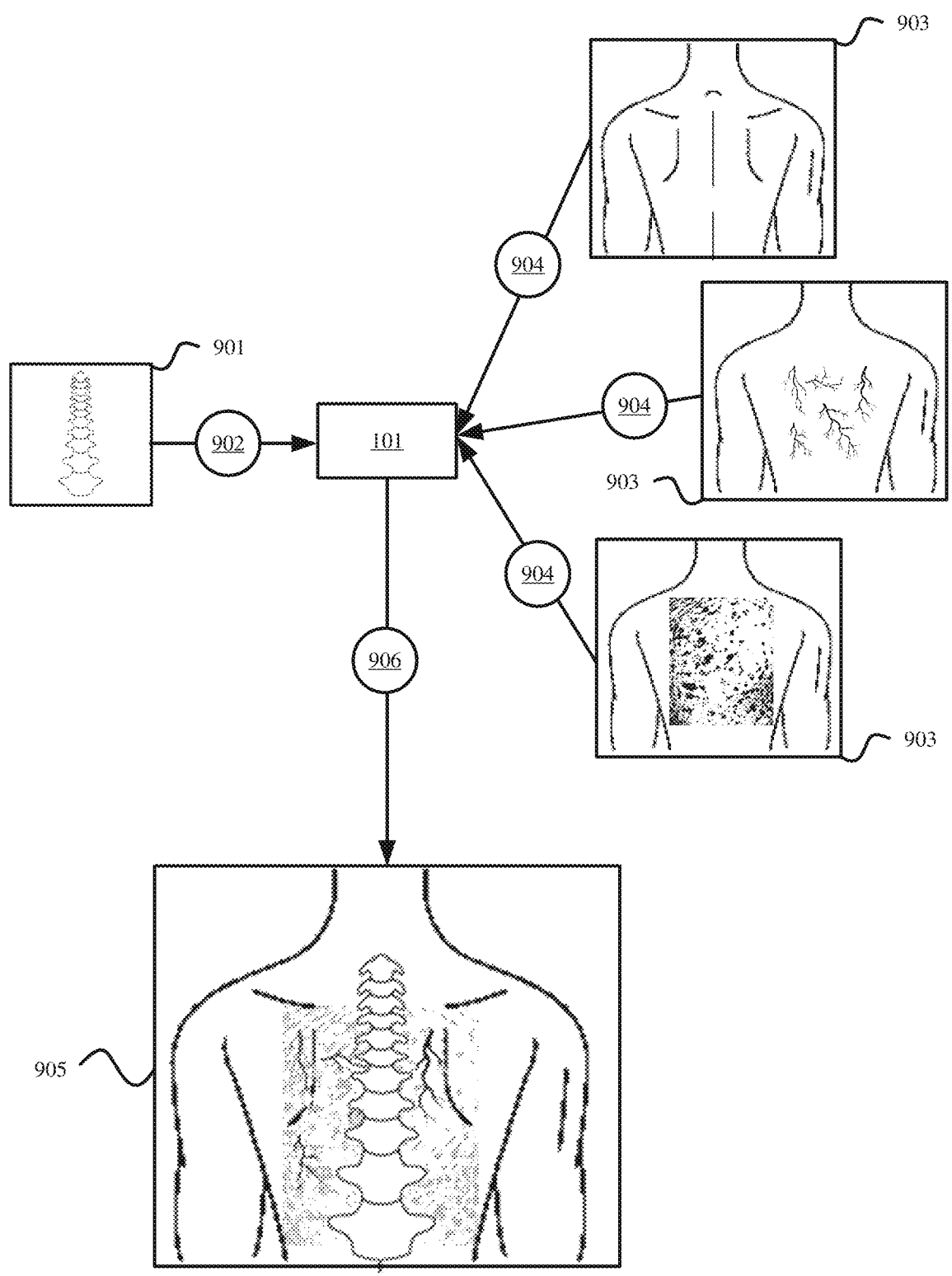
FIG. 9 illustrates an example of enhancing a first image by mapping multispectral properties, that are obtained from a second set of images, onto first image in accordance with some embodiments presented herein.

FIG. 9 illustrates an example of imaging device 101 enhancing a first image 901 by mapping multispectral properties, that are obtained from second set of images 903, onto first image 901 in accordance with some embodiments presented herein. As shown in FIG. 9, first image 901 may be an image of a patient's spine. Imaging device 101 may receive (at 902) first image 901 from a different medical imaging device (e.g., an X-ray machine) in order to enhance first image 901 with multispectral data of the patient's back from which the medical practitioner may identify a precise location on the patient's spine.

Imaging device 101 may generate (at 904) a point cloud representation of the patient's back based on depth information and/or multispectral properties captured with second set of images 903. Imaging device 101 may map the point cloud data points onto first image 901 by referencing the data point depth information to identify protrusions and/or thicker density of the spine, and by aligning those data points exactly with corresponding features in first image 901. Imaging device 101 may generate (at 906) composite image 905 to overlay or enhance first image 901 with the multispectral data from the point cloud. The medical practitioner may use several reference points provided by the multispectral data of composite image 905 to determine how to best access the precise location on the patient's spine.

Figure 10:
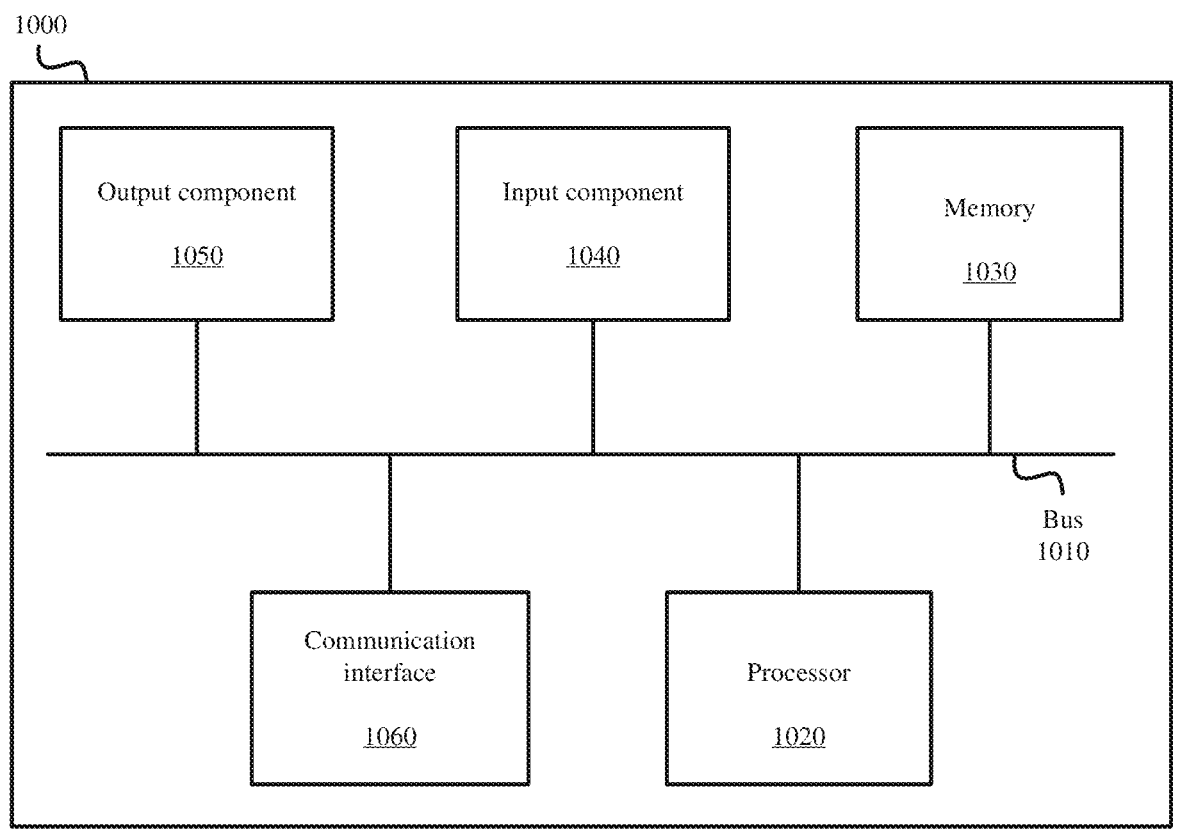
FIG. 10 illustrates example components of one or more devices, according to one or more embodiments described herein.

FIG. 10 is a diagram of example components of device 1000. Device 1000 may be used to implement one or more of the devices or systems described above (e.g., imaging device 101). Device 1000 may include bus 1010, processor 1020, memory 1030, input component 1040, output component 1050, and communication interface 1060. In another implementation, device 1000 may include additional, fewer, different, or differently arranged components.

Bus 1010 may include one or more communication paths that permit communication among the components of device 1000. Processor 1020 may include a processor, microprocessor, or processing logic that may interpret and execute instructions. Memory 1030 may include any type of dynamic storage device that may store information and instructions for execution by processor 1020, and/or any type of non-volatile storage device that may store information for use by processor 1020.

Input component 1040 may include a mechanism that permits an operator to input information to device 1000, such as a keyboard, a keypad, a button, a switch, etc. Output component 1050 may include a mechanism that outputs information to the operator, such as a display, a speaker, one or more light emitting diodes ("LEDs"), etc.

Communication interface 1060 may include any transceiver-like mechanism that enables device 1000 to communicate with other devices and/or systems. For example, communication interface 1060 may include an Ethernet interface, an optical interface, a coaxial interface, or the like. Communication interface 1060 may include a wireless communication device, such as an infrared ("IR") receiver, a Bluetooth® radio, or the like. The wireless communication device may be coupled to an external device, such as a remote control, a wireless keyboard, a mobile telephone, etc. In some embodiments, device 1000 may include more than one communication interface 1060. For instance, device 1000 may include an optical interface and an Ethernet interface.

Device 1000 may perform certain operations relating to one or more processes described above. Device 1000 may perform these operations in response to processor 1020 executing software instructions stored in a computer-readable medium, such as memory 1030. A computer-readable medium may be defined as a non-transitory memory device. A memory device may include space within a single physical memory device or spread across multiple physical memory devices. The software instructions may be read into memory 1030 from another computer-readable medium or from another device. The software instructions stored in memory 1030 may cause processor 1020 to perform processes described herein. Alternatively, hardwired circuitry may be used in place of or in combination with software instructions to implement processes described herein. Thus, implementations described herein are not limited to any specific combination of hardware circuitry and software.

The foregoing description of implementations provides illustration and description, but is not intended to be exhaustive or to limit the possible implementations to the precise form disclosed. Modifications and variations are possible in light of the above disclosure or may be acquired from practice of the implementations.

The actual software code or specialized control hardware used to implement an embodiment is not limiting of the embodiment. Thus, the operation and behavior of the embodiment has been described without reference to the specific software code, it being understood that software and control hardware may be designed based on the description herein.

For example, while series of messages, blocks, and/or signals have been described with regard to some of the above figures, the order of the messages, blocks, and/or signals may be modified in other implementations. Further, non-dependent blocks and/or signals may be performed in parallel. Additionally, while the figures have been described in the context of particular devices performing particular acts, in practice, one or more other devices may perform some or all of these acts in lieu of, or in addition to, the above-mentioned devices.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

Further, while certain connections or devices are shown, in practice, additional, fewer, or different, connections or devices may be used. Furthermore, while various devices and networks are shown separately, in practice, the functionality of multiple devices may be performed by a single device, or the functionality of one device may be performed by multiple devices. Further, while some devices are shown as communicating with a network, some such devices may be incorporated, in whole or in part, as a part of the network.

To the extent the aforementioned embodiments collect, store or employ personal information provided by individuals, it should be understood that such information shall be used in accordance with all applicable laws concerning protection of personal information. Additionally, the collection, storage and use of such information may be subject to consent of the individual to such activity, for example, through well-known "opt-in" or "opt-out" processes as may be appropriate for the situation and type of information. Storage and use of personal information may be in an appropriately secure manner reflective of the type of information, for example, through various encryption and anonymization techniques for particularly sensitive information.

Some implementations described herein may be described in conjunction with thresholds. The term "greater than" (or similar terms), as used herein to describe a relationship of a value to a threshold, may be used interchangeably with the term "greater than or equal to" (or similar terms). Similarly, the term "less than" (or similar terms), as used herein to describe a relationship of a value to a threshold, may be used interchangeably with the term "less than or equal to" (or similar terms). As used herein, "exceeding" a threshold (or similar terms) may be used interchangeably with "being greater than a threshold," "being greater than or equal to a threshold," "being less than a threshold," "being less than or equal to a threshold," or other similar terms, depending on the context in which the threshold is used.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items, and may be used interchangeably with the phrase "one or more." Where only one item is intended, the terms "one," "single," "only," or similar language is used. Further, the phrase "based on" is intended to mean "based, at least in part, on" unless explicitly stated otherwise.

What is claimed is:

1. A method comprising:
    capturing visible properties of a received work revealed by a first range of electromagnetic spectrum;
    capturing non-visible properties of the received work revealed by a second range of electromagnetic spectrum;
    determining a texture of a particular material about an outer surface of the received work from the non-visible properties;
    detecting a number of layers applied over the particular material at different points across the outer surface of the received work based on the non-visible properties;
    determining an amount of deviation between the received work and a reference image, against which to authenticate the received work, based on differences between the visible properties, the texture, and the number of layers at different points across the outer surface of the received work and corresponding points of the reference image; and
    verifying authenticity of the received work in response to the differences between the visible properties, the texture, and the number of layers across each of the received work and the reference image being within a defined threshold.

2. The method of claim 1, wherein verifying the authenticity comprises:
    determining that the received work is not an original work in response to the differences in the visible properties being within a first threshold and the differences in the texture and the number of layers being outside a second threshold; and
    authenticating the received work as the original work in response to the differences in the visible properties being within the first threshold and the differences in the texture and the number of layers being within the second threshold.

3. The method of claim 1 further comprising:
    defining the reference image based on visible and non-visible properties of materials used by one or more machines creating authorized reproductions of an original work; and
    wherein verifying the authenticity comprises:
        determining that the received work is not one of the authorized reproductions in response to one or more of the visible properties and the non-visible properties of the received work not matching the visible and non-visible properties of the materials used by the one or more machines; and
        verifying that the received work is one of the authorized reproductions in response to the visible properties and the non-visible properties of the received work matching the visible and non-visible properties of the materials used by the one or more machines.

4. The method of claim 1 further comprising:
    defining the reference image based on a patterning of visible and non-visible properties produced by one or more machines; and wherein verifying the authenticity comprises:
  determining that the received work is not created by the one or more machines in response to patterning of one or more of the visible properties and the non-visible properties of the received work not matching the patterning of the visible and non-visible properties produced by the one or more machines; and
  verifying that the received work is created by the one or more machines in response to patterning of the visible properties and the non-visible properties of the received work matching the patterning of the visible and non-visible properties produced by the one or more machines.

5. The method of claim 1 further comprising:
exposing an original work to the first range of electromagnetic spectrum;
capturing visible properties of the original work revealed by the first range of electromagnetic spectrum;
exposing the original work to the second range of electromagnetic spectrum;
capturing non-visible properties of the original work revealed by the second range of electromagnetic spectrum; and
generating the reference image by combining the visible properties of the original work with the non-visible properties of the original work into a single composite image.

6. The method of claim 1,
wherein the first range of the electromagnetic spectrum corresponds to a visible light spectrum; and
wherein the second range of the electromagnetic spectrum corresponds to a non-visible light spectrum comprising one or more of an ultraviolet spectrum, an X-ray spectrum, and an infrared spectrum.

7. The method of claim 1,
wherein capturing the visible properties of the received work comprises mapping color attributes across a non-uniform surface layer of the received work; and
wherein capturing the non-visible properties of the received work comprises:
  measuring variations in the second range of electromagnetic spectrum measured at different points across the non-uniform surface layer; and
  mapping the variations to determine the texture and the number of layers.

8. The method of claim 1,
wherein determining the texture comprises detecting variations in one of ultraviolet spectrum, X-ray spectrum, and infrared spectrum; and
wherein detecting the number of layers comprises detecting variations in another of the ultraviolet spectrum, X-ray spectrum, and infrared spectrum.

9. The method of claim 1,
wherein capturing the visible properties of the received work comprises mapping color attributes across a non-uniform surface layer of the received work; and
wherein detecting the number of layers comprises mapping different variations in the second range of electromagnetic spectrum at the different points to different numbers of layers at the different points.

10. The method of claim 1 further comprising:
wherein capturing the visible properties of the received work comprises configuring a first filter that permits the first range of electromagnetic spectrum onto a sensor and that blocks the second range of electromagnetic spectrum from the sensor; and
wherein capturing the non-visible properties of the received work comprises configuring a second filter that permits the second range of electromagnetic spectrum onto the sensor and that blocks the first range of electromagnetic spectrum from the sensor.

11. The method of claim 1 further comprising:
generating the reference image at a first time prior to lending an original work to a third-party; and
wherein verifying the authenticity comprises confirming return of the original work at a second time based on the differences being within the threshold.

12. The method of claim 1 further comprising:
generating a point cloud comprising a plurality of data points that are positioned in a three-dimensional ("3D") space to represent positions of different points of the received work;
wherein capturing the visible properties comprises mapping the visible properties at each particular point of the received work to a data point of the plurality of data points with a same position as the particular point; and
wherein capturing the non-visible properties comprises mapping the non-visible properties at each particular point of the received work to a data point of the plurality of data points with a same position as the particular point.

13. A system for authenticating different works, the system comprising:
one or more processors configured to:
  capture visible properties of a received work revealed by a first range of electromagnetic spectrum;
  capture non-visible properties of the received work revealed by a second range of electromagnetic spectrum;
  determine a texture of a particular material about an outer surface of the received work from the non-visible properties;
  detect a number of layers applied over the particular material at different points across the outer surface of the received work based on the non-visible properties;
  determine an amount of deviation between the received work and a reference image, against which to authenticate the received work, based on differences between the visible properties, the texture, and the number of layers at different points across the outer surface of the received work and corresponding points of the reference image; and
  verify authenticity of the received work in response to the differences between the visible properties, the texture, and the number of layers across each of the received work and the reference image being within a defined threshold.

14. The system of claim 13, wherein verifying the authenticity comprises:
determining that the received work is not an original work in response to the differences in the visible properties being within a first threshold and the differences in the texture and the number of layers being outside a second threshold; and
authenticating the received work as the original work in response to the differences in the visible properties being within the first threshold and the differences in the texture and the number of layers being within the second threshold.

15. The system of claim 13, wherein the one or more processors are further configured to:

define the reference image based on visible and non-visible properties of materials used by one or more machines creating authorized reproductions of an original work; and wherein verifying the authenticity comprises:
determining that the received work is not one of the authorized reproductions in response to one or more of the visible properties and the non-visible properties of the received work not matching the visible and non-visible properties of the materials used by the one or more machines; and verifying that the received work is one of the authorized reproductions in response to the visible properties and the non-visible properties of the received work matching the visible and non-visible properties of the materials used by the one or more machines.

16. The system of claim 13, wherein the one or more processors are further configured to:

define the reference image based on a patterning of visible and non-visible properties produced by one or more machines; and wherein verifying the authenticity comprises:
determining that the received work is not created by the one or more machines in response to patterning of one or more of the visible properties and the non-visible properties of the received work not matching the patterning of the visible and non-visible properties produced by the one or more machines; and verifying that the received work is created by the one or more machines in response to patterning of the visible properties and the non-visible properties of the received work matching the patterning of the visible and non-visible properties produced by the one or more machines.

17. The system of claim 13, wherein the one or more processors are further configured to:

expose an original work to the first range of electromagnetic spectrum;

capture visible properties of the original work revealed by the first range of electromagnetic spectrum;

expose the original work to the second range of electromagnetic spectrum;

capture non-visible properties of the original work revealed by the second range of electromagnetic spectrum; and generate the reference image by combining the visible properties of the original work with the non-visible properties of the original work into a single composite image.

18. A non-transitory computer-readable medium, storing a plurality of processor-executable instructions to:

capture visible properties of a received work revealed by a first range of electromagnetic spectrum;

capture non-visible properties of the received work revealed by a second range of electromagnetic spectrum;

determine a texture of a particular material about an outer surface of the received work from the non-visible properties;

detect a number of layers applied over the particular material at different points across the outer surface of the received work based on the non-visible properties determine an amount of deviation between the received work and a reference image, against which to authenticate the received work, based on differences between the visible properties, the texture, and the number of layers at different points across the outer surface of the received work and corresponding points of the reference image; and verify authenticity of the received work in response to the differences between the visible properties, the texture, and the number of layers across each of the received work and the reference image being within a defined threshold.

19. The method of claim 1 further comprising:
defining the threshold based in part on tolerances of an imaging device used in said capturing of the visible properties and the non-visible properties of the received work.

* * * * *